US00PP09429P

United States Patent [19]

Jepsen

[11] Patent Number: Plant 9,429

[45] Date of Patent: Jan. 16, 1996

[54] KALANCHOË PLANT NAMED 'FAME'

[75] Inventor: Knud Jepsen, Hinnerup, Denmark

[73] Assignee: Knud Jepsen A/S, Hinnerup, Denmark

[21] Appl. No.: 376,390

[22] Filed: Jan. 23, 1995

[51] Int. Cl.[6] ..... A01H 5/00

[52] U.S. Cl. ..... Plt./87.15

[58] Field of Search ..... Plt./87.15

*Primary Examiner*—James R. Feyrer
*Attorney, Agent, or Firm*—Foley & Lardner

[57] ABSTRACT

A Kalanchoë plant named Fame particularly characterized by its large, luminous and orange flowers; grayish small leaves; uniform growth; and good keeping quality.

1 Drawing Sheet

The present invention relates to a new and distinct cultivar of Kalanchoë plant, botanically known as Kalanchoë, and referred to by the cultivar name Fame.

The new cultivar was referred to during the breeding and selection process by the designation No. KJ 5/87 and is a product of a planned breeding program. The basic objective of the breeding program was to create a new Kalanchoë cultivar having larger flowers, smaller leaves and more luminous orange color.

The new cultivar was originated from a cross made in a controlled breeding program in Hinnerup, Denmark. The female or seed parent was a proprietary cultivar designated 2/85 and the male or pollen parent was a proprietary cultivar designated 22/85.

Fame was discovered and selected by the inventor, Knud Jepsen, as a flowering plant within the progeny of the stated cross in a controlled environment in Hinnerup, Denmark.

Fame was first asexually reproduced by the inventor by stem cuttings in April 1987 in Hinnerup Denmark. Asexual reproduction of the new cultivar by stem cuttings, as performed by the inventor in Hinnerup, Denmark has demonstrated that the combination of characteristics as herein disclosed for the new cultivar are firmly fixed and retained through successive generations of asexual reproduction.

Fame has not been observed under all possible environmental conditions. The phenotype may vary with variations in environment such as temperature, light intensity and day length without a change in genotype. The following observations, measurements and values describe the new cultivar as grown in Hinnerup, Denmark under greenhouse conditions which closely approximate those generally used in commercial practice.

The following traits have been repeatedly observed and are determined to be basic characteristics of Fame, which in combination, distinguish this Kalanchoë as a new and distinct cultivar:

1. Large and luminous orange flowers.
2. Grayish small leaves.
3. Uniform growth.
4. Good keeping quality.

Fame is principally distinguished from other kinds of orange Kalanchoë plants by its more luminous and desirable color and larger flowers.

The accompanying photographic drawings show a typical specimen plant of the new cultivar. The colors appearing in the photograph are as true as possible with color illustrations of this type. Photo:

Figure 1:
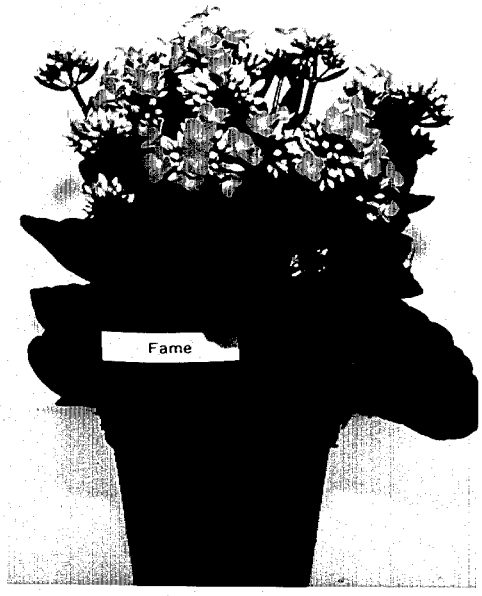
FIG. 1 is a sideview of the specimen plant showing the large and luminous orange flowers and grayish leaves.
Figure 2:
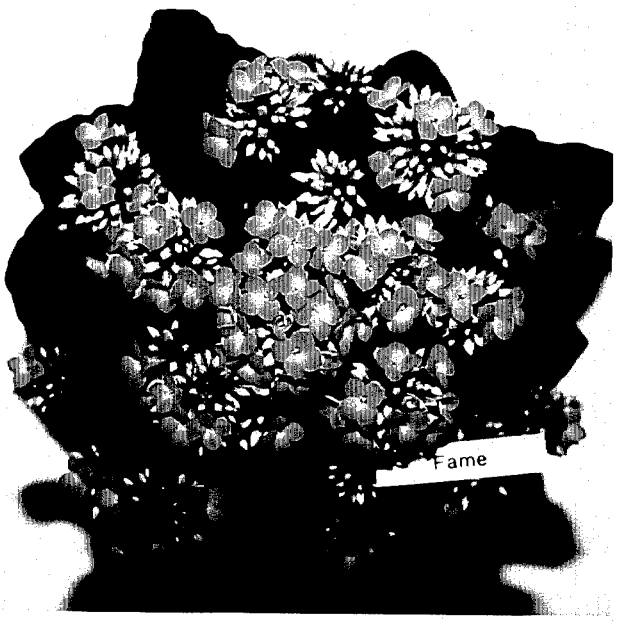
FIG. 2 is a topview of the specimen plant showing the flowers in greater detail.
Figure 3:
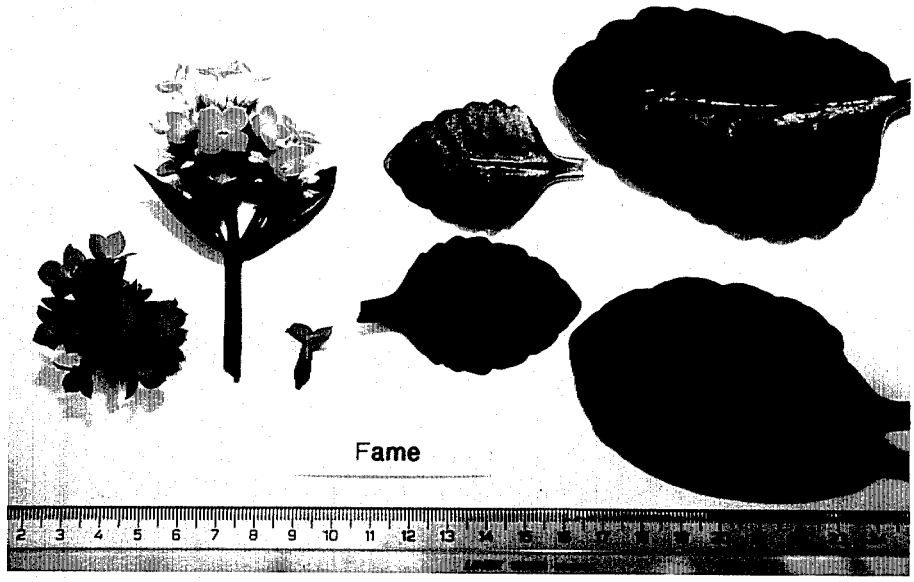
FIG. 3 is a close-up of the flowers and leaves.

In the following description, color references are made to The Royal Horticultural Society Colour Chart (R.H.S.), except where general colors of ordinary significance are referred to. Color values were taken under diffuse natural light conditions on a overcast day with blitz approximately 12:00 a.m. in Hinnerup, Denmark.

Botanical classification:

*Commerical.*—Kalanchoë cv. Fame.

Parentage:

*Male parent.*—22/85 (seedplant).

*Female parent.*—2/85 (seedplant).

Propagation: The new cultivar holds its distinguishing characteristics through successive propagations by leaf cuttings and by division of shoots.

*Type cutting.*—Top shoot.

*Time to root.*—Ten (10) days.

*Rooting habit.*—Branched roots produced from callus.

Plant description:

*Form.*—Compact plant. Height ca. 25 cm. Diameterca. 20 cm.

Habit of growth.—Upright growth, medium internodes, short and upright flowering shoots.

*Foliage description.*—Small leaves with short petioles. The leaf size is reduced when the floral stage is induced. Size: Vegetative leaves are approximately 10.5 cm×7 cm. The leaves produced by flowering plants are approximately 7. 5 cm×4.5 cm. Shape: Oval with an obtuse leaf tip. Texture: Glabrous. Margin: Undulate. Color: Young foliage: (topside): R.H.S. 137B. (underside: R.H.S. 137C. Mature foliage: (topside): R.H.S. 139A. (underside): R.H.S. 137C.

Flowering description:

Flowering habit.—Flowering is induced by short day length. Cymes are formed.

*Natural flowering season.*—Winter and spring. Flowering time under controlled day length at 20° C. in summer is eight (8) weeks. In winter (with artificial lighting) at 20° C. in the flowering time is nine (9) weeks.

*Flower buds.*—Dusty orange bud color, R.H.S. 35A. Size: 1.5 cm×0.4 cm just before anthesis. Shape: Chubby. Rate of opening: 50% open 1.5 weeks after first open flower.

*Flowers borne.*—The flowers are borne in dishasial cymes developing from leaf axils. The main inflorescences are branched into one central and 2–4 minor cymes during development.

*Quantity of flowers.*—10–15 headbunches with 30–50 flowers in 15–30 secondary bunches with 10–15 flowers (unpinched plants).

*Petals.*— Shape: Rounded obovate with cuspidate leaf tips. Color: Topside when opening: R.H.S. 32A, fading to R.H.S. 33 A. Underside: R.H.S. 34B. Number and size of petals: Four (4). Size of flowers: The petals measure 0.8 cm in diameter and the total flower diameter 2.1 cm.

*Reproductive organs.*— Stamens: Eight (8) in number. Anthers shape: Slightly oblong. Filament color: Yellow/green. Pollen color: Yellow. Pistils: Stigma: Round. Style color: White. Ovaries: Four (4) ovaries each measuring 0.5 cm×0.1 cm. The ovaries are light green and superior (hypogonous).

Disease resistance: No known Kalanchoë diseases observed to date. Resistance not observed.

General observations: Fame produces high-quality plants without pinching when grown in 9–10 cm pots with one cutting per pot. For larger 12 cm pots high-quality plants are produced when three cuttings or one pinched cutting is used per pot.

It is claimed:

1. A new and distinct Kalanchoë plant named Fame, as described and illustrated.

* * * * *